United States Patent [19]
DeLuca et al.

[11] Patent Number: 6,093,421
[45] Date of Patent: Jul. 25, 2000

[54] MACA AND ANTLER FOR AUGMENTING TESTOSTERONE LEVELS

[75] Inventors: Daryl L. DeLuca, Sugar Land; William S. Sparks, Bellaire; Denis R. DeLuca, Katy, all of Tex.

[73] Assignee: Biotics Research Corporation, Rosenberg, Tex.

[21] Appl. No.: 09/387,371

[22] Filed: Aug. 31, 1999

[51] Int. Cl.[7] .......................... A61K 35/36; A61K 35/32; A61K 35/78

[52] U.S. Cl. ........................ 424/543; 424/549; 424/195.1

[58] Field of Search ...................................... 424/549, 543, 424/572, 195.1, 811

[56] References Cited

U.S. PATENT DOCUMENTS

| | | | |
|---|---|---|---|
| 4,614,532 | 9/1986 | Schwamborn et al. | 71/92 |
| 5,408,041 | 4/1995 | Mundy et al. | 530/414 |

*Primary Examiner*—Jean C. Witz
*Attorney, Agent, or Firm*—John R Casperson

[57] ABSTRACT

Testosterone levels in men are increased by the oral administration of powdered maca and antler.

5 Claims, No Drawings

MACA AND ANTLER FOR AUGMENTING TESTOSTERONE LEVELS

BACKGROUND OF THE INVENTION

In one aspect, the invention relates to a dietary supplement to increase testosterone levels, especially in humans. In another aspect, the invention relates to increasing plasma testosterone levels using a combination of the edible Andean tuber (*Lepidium meyenii*), commonly known as maca, with deer or elk antler.

For a number of reasons, elevated testosterone levels are associated with sense of enhanced well-being in men.

Total testosterone levels decline with aging, about 0.2% per year in men, and testosterone replacement therapy has been used to improve the status of this hormone. A number of botanical preparations have been used to restore erectile function, including ginseng, Ginkgo biloba, yohimbine (*Pausinytalia yohimbe*), and muira puama (*Ptychopetoalum olacoides*) a South American plant. L-arginine, as a precursor of nitric oxide, and androstenedione also have application in male sexual function.

Maca (*Lepidium meyenii*) is a tuber cultivated in the Andean region, especially Peru, where it is a food staple. As reported in Dini et al., (Dini A., Miguliuolo G, Rastrelli L, et al. Chemical composition of Lepidium meyenii, *Food Chemistry* 1994;49:347–9) and Walker (Walker M, Effect of Peruvian Maca on hormonal functions. *Townsend Letter for Physicians* 1998; November: 18–21), the tuber is also used in folk medical traditions as a mood enhancer, as an antidepressant, and to promote wound healing. Dini et al. also reports that the chemical composition of Maca includes a balanced protein compared to carrot and potato protein.

Maca also contains a variety of trace minerals, including iron, copper and iodine as well as saponins and alkaloids.

A synopsis of a book by Gloria Chacon de Popivici, "La importanica de Lepidium peruvianum Chacon (Maca) en la Alimentacion y Salud del ser Humano y Animal 2,000 Ados Antes y Despues de Cristo y en el Siglo XXI", describes an experiment in which rats given maca powdered root had higher sperm production and motility rates than in control groups. The author is quoted as saying the alkaloids of maca affect the pituitary and hypothalamus, and it acts on adrenals, pancreas and thyroid. Along these lines, anecdotal information is available suggesting that maca alleviates perimenopausal and post menopausal symptoms, male impotence erectile dysfunction, and female and male sterility, healing bone fractures, osteoporosis, premature aging, and chronic fatigue.

Several books and reports describe Andean roots and tubers as crops and sources of food and beverage. See Soensen et al., (Soensen M, Gruneberg W J, Orting B et al. *Andean Roots and Tubers: ahipa, arracacha, maca and yacon*. Centro Intemaciojoal de la Papa, Lima Peru, 1997—Abstract); Condesan, (Pocket guide to nine exotic Andean roots and tubers. Lima, Peru. 1997. Abstract); Comas et al, (Comas M, Miquel X, de la Torre MC, Arias G. Estudio bromatoglogico de la maca o paca (*Lepdium meyenii*). *Alimentaria* 1997, no. 286:85–90. Abstract); Toledo et al., (Toledo J, Dehal P, Jarrin F et al. Genetic variability of Lepidium meyenii and other Andean Lepidium species assessed by molecular markers. *An. Botany* 1998;82:523–30. (Abstract). However, based on the information in the Abstracts, none of these references discuss the response of male hormone levels to ingestion of maca.

Elk antler has been analyzed chemically. See Batchelder H J. Velvet antler: a review of the literature, and Sunwoo H H, et al. Chemical composition of antlers from wapiti (*Cervus elaphus*). *J Agr Food Chem* 1995;43:2846–2849. Antler contains protein, sulfated glycosaminoglycans, and calcium, phosphorus and magnesium. Alpha linolenic acid is also present in the lipid fraction. Most of the glycosaminoglycans are in the form of chondroitin sulfates. See Sunwoo H H, et al. Glycosaminoglycans from growing antlers of wapiti (*Cervus elaphus*). *Can J Animal Sci* 1997;77:715–21.

Epidermal growth factor has been isolated from velvet antler of red deer (*Cervus elaphus*). Ko K M, et al. Epidermal growth factor from deer *Cervus elaphus* submaxillary and velvet antler. *Gen Comp Endocrinol* 1986;63:431–40. (Abstract)

Also, velvet antler total peptides were shown to stimulate proliferation of chondrocytes from rabbit and human fetus in a study by Zhou et al. (Zhou Q-L, et al. Velvet antler polypeptides promoted proliferation of chondrocytes and osteoblast precursors and fracture healing. *Acta Pharm Sinica* 1999;20:279–82).

Chen et al., (Chen X, et al. "Inhibitor effects of the extract of pilose antler on monamine oxidase in aged mice" *Chum Kuo Chung Yao Tsa Chih* 1992;17:107–28—Abstract) reported that antler extract inhibited monamine oxidase activity in mouse liver.

Kum et al (Kum H S, et al. Inhibitory effects of velvet antler water extract on morphine-induced conditioned place preference and DA receptor supersensitivity in mice. *J Ethnopharmacology* 1999;66:25–31) reported that administration of water extract of elk antler to mice prior to morphine treatment prevented the development of morphine-induced behavior and polysynaptic DA receptor supersensitivity.

Ahn (Ahn B H., Study on the nutritive value of velvet antler by major processing districts. *Korean J Animal Nutr* 1994;18:173–8. Abstract) reported that crude protein from velvet antler did not affect weight gain, food intake in rats, but supplementation lowered blood cholesterol.

Wang (Wang B X, et al. Stimulating effect of deer antler extract on protein synthesis in senescence acceeleated mice in vivo. *Chem Pharm Bull* (Tokyo) 1988;36:2593–8. Abstract) reported that deer antler extract stimulated protein synthesis in senescence accelerated mice.

Zhang (Zhang Z Q, et al. [Antiinflammatory effects of pilose antler peptide] *Chung Kuo Yao Li Hsueh Pao* 1994;15:282–4. (Abstract)) reported that a 7200 dalton peptide isolated from deer antler inhibited chronic and acute inflammation in rats.

A Russian report (Yartsev V G. Residual adaptogenic and antistress activities of pharmacoepeial preparations from velvet antlers and from waste of their pharmaceutical processing. *Farmatsiya* (Mosc) 1991;40:47–51. (abstract)) noted that antlers of Manchurina, rein, and sika deer contain substances that promote adaptation to stress and that waste products from manufacture of antler supplements can fatten pigs and chickens. Another Russian report (Vereshchagin A, et al. On the standardization of the Pantocrin preparation. 1. Evaluating antihypertensive activity of its individual components. *Khimiko-Farmatsevticheskii Zhurnal* 1997;31:53–6. (Abstract)) suggests that pharmaceutical grade deer antler preparation Pantocrin lowers elevated blood pressure In Chinese medicine, deer antler is used in a variety of remedies. However, there is little documentation in the medical literature to support this usage. The long term safety has not been studied. See. Dalefield R E, Oehme F W. Deer velvet antler: some unanswered questions. *Veterinary and Human Toxicology* 1999;41:39–41.

One unpublished study (Fischer, B D, et al. Strength training parameters in the Edmonton Police Force following supplementation with elk velvet antler. Report, University of Alberta, Dec. 11, 1998) noted that when men were administered elk velvet antler for more than 3 weeks, there was a 5–6 fold increase in blood plasma testosterone levels. The amounts of elk velvet antler ingested, the duration of the study and the numbers of subjects were not specified in that report, nor were data presented to support this conclusion, however.

OBJECTS OF THE INVENTION

It is an object of this invention to provide a treatment to increase testosterone levels and to provide a sense of enhanced well-being in men.

SUMMARY OF THE INVENTION

We have found that a combination of the Andean tuber, maca, and antler, such as from deer or elk, is useful in raising testosterone levels in men with low normal or low testosterone levels, while enhancing vitality.

DETAILED DESCRIPTION OF THE INVENTION

In accordance with an embodiment of the invention, we have demonstrated that a combination of powdered maca and powdered deer antler is capable of increasing plasma testosterone levels in men between the ages of 45 and 55.

Preferably, the maca is from a tuber of *Lepidium meyenii* and the antler is from an artiodactyl animal, preferably deer or elk and most preferably antler in the velvet stage.

The powdered maca and antler are administered at a weight ratio of maca to antler which is generally in the range of about 1:1 to about 100:1, preferably together in admixture at a weight ratio in the range of about 5:1 to about 50:1.

The combination is preferably administered orally, as an admixture of maca and antler in powdered form, more preferably in the form of a tablet or capsule which consists essentially of the admixture. The tablet or capsule can be taken as a dietary supplement, alone or in combination with other foods.

The combination is preferably administered in the form of tablets or capsules which contain both maca and antler. The maca tuber content will generally range from 100 mg to 10 g and the antler content will generally range from 10 mg to 1 g. Preferably, the maca tuber content will be in the range of 250 mg to 2.5 g and the antler content will be in the range of 25 mg to 250 mg. A convenient amount of the combination for capsules or tablets is about 750 mg maca powder and about 50 mg powdered antler.

Male patients with low or low normal testosterone levels are treated with the combination in the amount of at least about 250 mg maca power and 25 mg of powdered antler daily. For quickly achieving increased testosterone levels, the patients can be treated with maca powder and powdered deer antler at an initial daily oral dosage in the range of 3 grams of maca or more and 200 mg of deer antler or more. This dosage level can be achieved by ingesting two of the above described capsules or tablets twice daily. The supplement may be taken orally, with meals or between meals. After about two weeks, the patients can be placed on a maintenance oral dosage of about 1.5 g of maca and 100 mg of deer antler daily. This dosage can be achieved by ingesting one capsule or tablet twice daily. Additional capsules can be taken if desired, for example, up to ten capsules or tablets daily.

The combination is generally administered to patients who have a first testosterone level at or beneath a normal range in an amount and for a period of time sufficient to cause the patient to have a second testosterone level which is higher than the first testosterone level and is within or slightly above the normal range. What is a normal range will vary depending on age and time of day, and may also vary depending on other factors. Good results have been obtained for patients in the age range of 45–55 years. For the sample group of patients, testosterone levels at least doubled after a time of treatment of at least two weeks, and generally increased in the range of 200% to 500% from initial levels.

In the sample study, five men between the ages of 45 and 55 years of age participated. Initial hormone levels were determined by means of a salivary cortisol testing. Testosterone levels in saliva reflect plasma free testosterone in standard test procedures. Because testosterone follows a circadian rhythm, morning and afternoon samples were analyzed.

After supplementation for 30 days, salivary testosterone levels were again determined. Testosterone levels increased in five of five subjects. All subjects had initial morning testosterone levels that were within the laboratory reference range, while subjects 1, 2, and 3 had afternoon testosterone levels that were below the reference range.

After the treatment described herein, all five patients tested had increased levels for morning and afternoon testosterone. For morning values, the mean increase was 274% (sd=116) with a range of 158% to 417% for n=5. For the afternoon values, the mean increase was 274% (sd=183) with a range of 116% to 474% for n=3.

The combination treatment increased testosterone levels above the laboratory reference range for morning testosterone in three of the five patients, although supplementation did not increase testosterone values greater than the reference range in the afternoon samples (n=3). Of interest is one patient follow up. Subject #1 abstained from the maca-antler supplement for 30 days after supplementation. In this subject, salivary testosterone levels dropped back to near base line.

A questionnaire elicited participan t response before and after supplementation. Based upon participant feedback, ingestion of the maca-antler combination often increased the energy level and sense of well-being in sample population.

The results are summarized in Table I.

TABLE I

Salivary Testosterone levels before and after 30 day supplementation with a combination of maca and velvet deer antler powder.

| Subject | initial | (Testosterone, pg/nil) supplementation 30 days | 30 day washout |
|---|---|---|---|
| #1 | am 48.1 | 120.7 (+251%) | 93.9 |
|  | pm 39.8 | 91.9 (231%) | 64.3 |
| #2 | am 52.8 | 137.0 (+260%) | — |
|  | pm 32.2 | 37.5 (116%) |  |
| #3 | am 45.5 | 168.0 (+369%) | — |
|  | pm 25.5 | 121.0 (+475%) |  |
| #4 | am 58.5 | 101.7 (+174%) | — |
| #5 | am 102.0 | 161.2 (+158%) | — |

While certain preferred embodiments of the invention are described herein, the invention is not to be construed as so limited, except to the extent that such limitations are found in the claims.

What is claimed is:

1. A process of increasing testosterone levels in a man comprising:

orally administering to a man in need of such a treatment, an effective amount of a composition containing maca and antler.

2. The process of claim 1 wherein the maca and antler are administered in tablet or capsular form, or in combination with food.

3. The process of claim 1 wherein at least about 250 mg of maca and 25 mg of antler is administered daily.

4. The process of claim 3 wherein the man is in the age range of 45–55 years.

5. The process of cliam 1 wherein a range of 1 to 10 g of maca and 100 mg to 1 g of antler is administered daily for a period of time of at least two weeks.

* * * * *